United States Patent [19]
Lucas

[11] 4,179,756
[45] Dec. 25, 1979

[54] GOGGLES

[76] Inventor: Charles Lucas, 3769 Dianne St., Bethpage, N.Y. 11714

[21] Appl. No.: 926,532

[22] Filed: Jul. 20, 1978

[51] Int. Cl.$^2$ ............................................. A61F 9/02
[52] U.S. Cl. .......................................... 2/434; 2/438; 2/441; 351/47; 351/57
[58] Field of Search ................. 2/434, 438, 9, 426, 2/427, 440, 441; 351/47, 57

[56] References Cited
U.S. PATENT DOCUMENTS

| | | | |
|---|---|---|---|
| 1,969,710 | 8/1934 | Jones | 2/438 |
| 2,719,972 | 10/1955 | Kelly | 2/8 |
| 2,846,684 | 8/1958 | Hill | 2/438 X |
| 3,389,406 | 6/1968 | Mitchell | 2/434 |
| 3,685,889 | 8/1972 | Thatcher | 351/47 |
| 3,752,567 | 8/1973 | Broadhurst | 351/57 X |

FOREIGN PATENT DOCUMENTS 871641 2/1953 Fed. Rep. of Germany ............. 351/47
218935 5/1942 Switzerland .................................. 2/434

*Primary Examiner*—Peter P. Nerbun
*Attorney, Agent, or Firm*—Michael I. Kroll

[57] ABSTRACT

A pair of goggles for protecting the eyes from contamination is provided having a plurality of sliding lenses in a frame so that when the outer most lens becomes dirty it is pushed down into the frame of the goggles leaving a clear view through the remaining lenses. Similarly when the next lens becomes dirty it also slides down leaving the remaining lenses in place, said procedure being repeated until all the movable lenses have been utilized.

4 Claims, 4 Drawing Figures

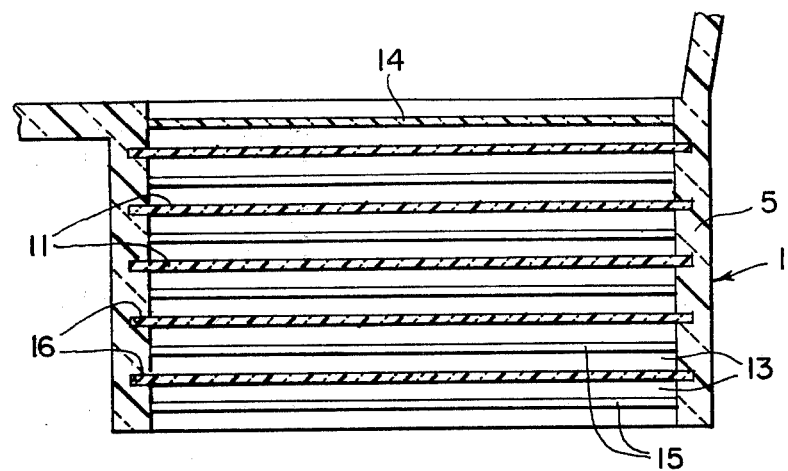
Fig. 2
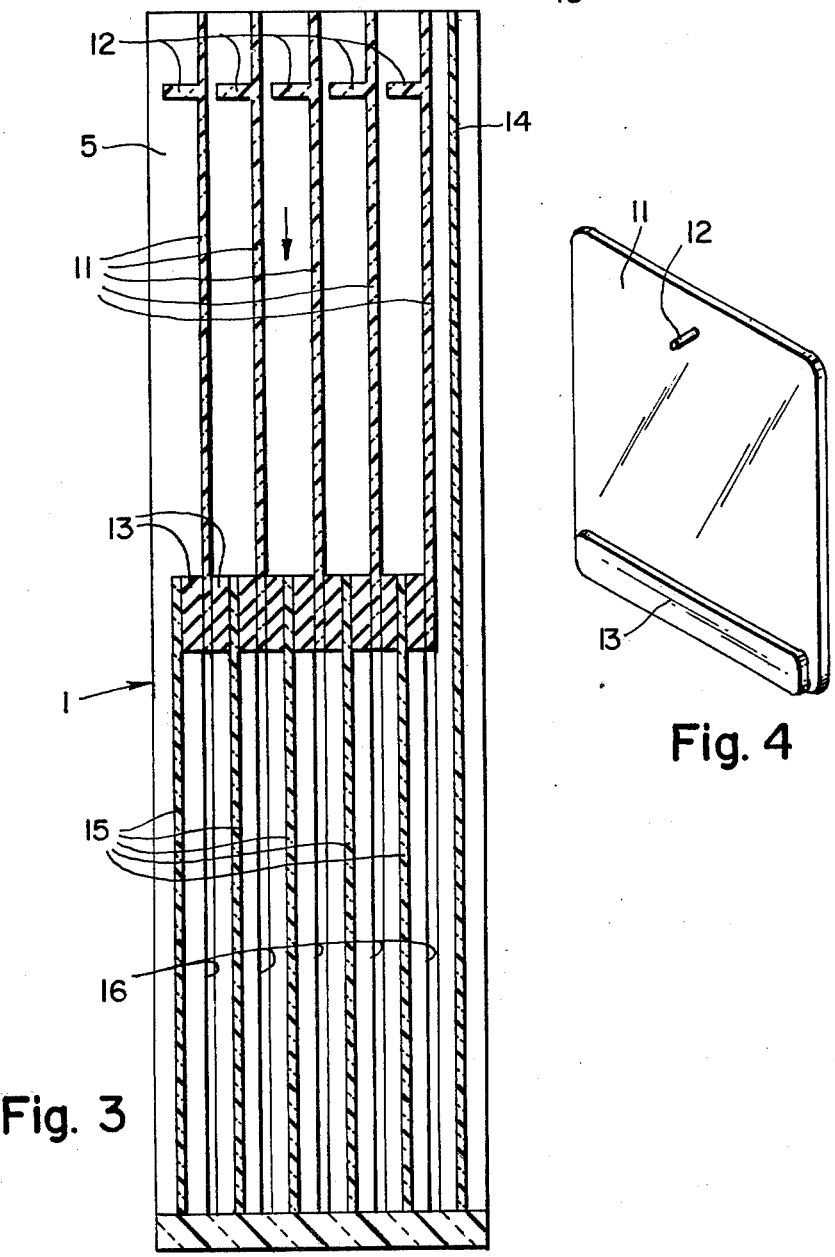
Fig. 4
Fig. 3

GOGGLES

BACKGROUND OF THE INVENTION

This invention relates to a pair of goggles for use by jockeys, harness drivers and alike to protect their eyes from foreign objects when they are riding in a race. Their eyes must be protected from general contamination which includes dust, dirt, mud and stones that are inherently present on race tracks. The race driver must be able to at all times have a clear range of vision unobstructed by debris that is deposited on the lenses of their goggles particularly when a race track is wet or muddy. In the past the user would have typically 6 pairs of goggles on his head at one time, each pair nested into the others such that when the outer most pair was contaminated the user would, with one hand, peel off that pair leaving the remaining 5 pairs in place. Similarly when the next pair of goggles were dirty it too would be removed leaving the remaining goggles. This procedure was repeated until there all the goggles were used.

Such procedure is very awkward as the user had to have six separate pair of goggles. Often times when the user attempted to remove only the contaminated goggles two or more goggles would be stuck together. Since the user could only use one hand to effect the goggle change the other hand always having to be on the reins of the horse, full utilization of the multigoggle arrangement was lost.

The instant invention eliminates the need for 6 separate goggles the total cost of which is rather expensive.

The instant invention permits simple and easy operation by the touch of a finger and can easily be used irrespective whether or not the operator is wearing gloves. The operator simply in a split second slides down the dirty lense exposing the remaining unobstructed lense.

SUMMARY OF THE INVENTION

It is therefore an object of this invention to provide an improved apparatus for protecting the eyes consisting of a plurality of lenses retained in a frame such that when the first lens becomes contaminated the lens may with one hand be pushed down and out of the sight of the user so that the user has a clear view through the remaining lenses.

Another object of this invention is to provide the lenses in frame such that the contaminated lenses may easily be removed for cleaning and replaced and reused.

A still further object of this invention is to provide an uncomplicated, inexpensive, useful, and reliable pair of goggles.

Briefly, one embodiment of this invention includes a frame adapted to fit over the users eyes with straps attached thereto and adapted so that the straps fit around the head of the user and holds the frame snuggly over the eyes. The frame retains a plurality of movable lenses mounted therein, each lense being kept in place by suitably provided friction guides.

A finger grip is attached to each movable viewing lens so that the operator may easily push down the viewing lenses as required. The slide down viewing lenses are retained in guide slots which provide sliding friction so that the viewing lens retains the desired position either in a viewing or non viewing position.

On either side of the slide down viewing lens there is affixed to the bottom most portion a gasket which contacts a plurality of stationary lenses so that the frame assembly becomes contamination tight.

The slide down viewing lenses may be removed for cleaning by means of opening the snap-on cover provided in the frame. These lenses may also be individually replaced if required at a minimum cost whereas in the multi-goggle arrangement the entire pair of goggles had to be disgarded if the viewing area became scratched.

BRIEF DESCRIPTION OF THE DRAWINGS

FIG. 2 is a sectional view, taken along the plane of line 2—2 in FIG. 1.

FIG. 3 is a sectional view, taken along the plane of line 3—3 in FIG. 1.

FIG. 4 is a perspective view of a slide down viewing lens.

DESCRIPTION OF THE PREFERRED EMBODIMENTS

Figure 1:
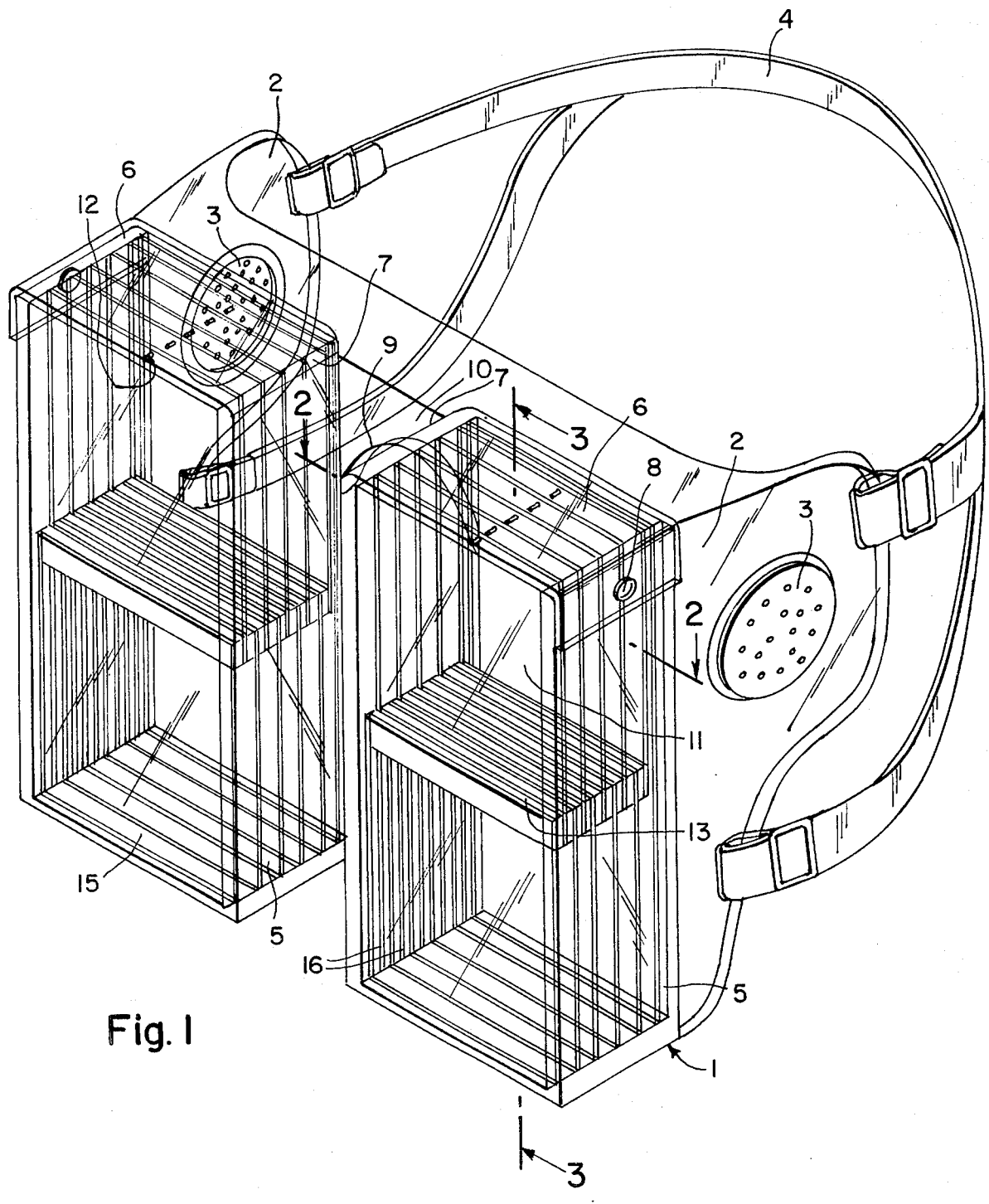
FIG. 1 is a perspective view of the invention.

With continuing reference to the accompanying drawings, wherein like reference numerals designate similar parts throughout the various views, reference 1 generally designates a frame housing of which two are provided, one for each eye, the two frame housings being affixed to each other by means of frame connector 10. Nose bridge 9 of frame connector 10 is provided such that it rests on the nose of the user. Transparent side of frame 2 is shaped so that it fits closely around the top of the eyebrow and temple to provide a snug fit on the user's head. Incorporated in the transparent side of the frame is air vent 3. The aforementioned structure is provided for on both sides of the structure. Adjustable elastic strap 4 is provided to securely hold the goggle assembly in place and attaches to the transparent side of the frame in 2 places.

As shown in FIG. 1, FIG. 2 and FIG. 3 each frame housing 1 in the preferred embodiment consists of a full length transparent stationary lens 14 which is ideally four and one quarter inches long by 2 inches wide and is securely fastened to frame housing 1, said full length transparent stationary lens located closest to the eye. Adjacent to full length transparent stationary lens 14 is positioned one of the transparent slide down viewing lenses 11 positioned initially in the upper most position the preferred size being two and one eight inches high by two inches wide. Attached to one side of the bottom most portion of 11 (FIG. 4) is soft gasket 13 with the preferred size of one and five eights inches long by one quarter inch high by one sixteenth inch thick; said soft gasket contacting stationary lens 15 initially at the uppermost section of the stationary lens. Adjacent to the first transparent slide down viewing lens 11 is a second transparent slide down viewing lens 11 with two soft gaskets 13 affixed on both sides of the bottom of the second transparent slide down viewing lens, one side of the soft gasket in contact with one side of the first stationary lens and the other soft gasket in contact with the next stationary lens.

The preferred number of transparent slide down viewing lenses is five and the preferred number of stationary lenses is also five although the number may vary. The lenses are typically one thirty-second of an inch thick although this too may vary.

Each transparent slide down viewing lens 11 is provided with a finger grip 12 so that the operator may easily position the transparent slide down viewing lens.

Frame housing 1 is provided with guide slots 16 so that the transparent slide down viewing lenses 11 will be retained. The slots are sized so that a slight friction is exerted onto the vertical edges of the transparent slide down viewing lenses so that these lenses will remain in the desired position whether it be in the upward or downward position.

The uppermost section of frame housing 1 is enclosed by snap-on cover 6. Hinge 7 is provided on one side of snap-on cover 6 and snap closure 8 engages transparent side of frame housing 5 to form an enclosure for the transparent slide down viewing lenses. The sides of frame housing is transparent so that the users side, top and bottom view is unobstructed. Transparent slide down viewing lens 11 and the full length transparent stationary lens 14 may be constructed from clear or tinted plastic with a preferred thickness of one thirty second inch.

In operation the five transparent slide down viewing lenses are in the upward position. As the lens furtherest from the users eyes becomes dirty the operator simply uses a finger and pushes finger grip 12 downward so that the lens guided by slot 16 is depressed into the lower most section of frame housing 1. Soft gasket 13 keeps foreign matter from contaminating the balance of the lenses. Similarly, when the next lens becomes contaminated it is pushed down leaving still another uncontaminated lens. The process is continued and there is provided a sufficient number of lenses to permit the user to complete a race with unimpared vision at all times.

The transparent slide down viewing lenses are easily removed by opening snap-on cover 6 and all the lenses, both the movable and stationary as well as the frame housing may be washed out and reused.

While the form of apparatus herein described constitutes a preferred embodiment of the invention, it is to be understood that the invention is not limited to this precise form of apparatus, and that changes may be made therein without departing from the scope of this invention.

Having regard to the foregoing the following is claimed:

1. An improved pair of goggles for protecting the users eyes from contamination of the type having a frame housing, a plurality of transparent slide down viewing lenses, a plurality of stationary lenses, means to keep contamination from entering the internal sections of the frame housing and lenses and means to keep the goggles on the users head wherein the improvement comprises;
    (a) a plurality of guide slots so that the contaminated transparent slide down viewing lenses may be guided downward and out of view of the users view; and
    (b) a snap-on cover to permit disassembly and reassembly of the transparent slide down viewing lenses to permit cleaning and replacement of the lenses.

2. A pair of goggles as recited in claim 1, in which the guide slots exert friction on the vertical edges of the transparent slide down viewing lenses to permit the lenses to remain in the desired position.

3. A pair of goggles as recited in claim 2, in which the frame housing is transparent to permit viewing through the frame housing at various angles of sight.

4. A pair of goggles as recited in claim 3, in which the transparent slide down viewing lenses are tinted to reduce glare.

* * * * *